United States Patent
Bianchi et al.

(10) Patent No.: US 9,718,947 B2
(45) Date of Patent: Aug. 1, 2017

(54) BIOTECHNOLOGICAL SULPHATED CHONDROITIN SULPHATE AT POSITION 4 OR 6 ON THE SAME POLYSACCHARIDE CHAIN, AND PROCESS FOR THE PREPARATION THEREOF

(75) Inventors: Davide Bianchi, Milan (IT); Marco Valetti, Seregno (IT); Paola Bazza, Villasanta (IT); Nicolò Miraglia, Buccinasco (IT); Ermanno Valoti, Dalmine (IT)

(73) Assignee: Gnosis S.p.A., Desio (IT)

( * ) Notice: Subject to any disclaimer, the term of this patent is extended or adjusted under 35 U.S.C. 154(b) by 582 days.

(21) Appl. No.: 13/270,435

(22) Filed: Oct. 11, 2011

(65) Prior Publication Data
US 2012/0289477 A1 Nov. 15, 2012

(30) Foreign Application Priority Data

May 12, 2011 (IT) .............................. MI2011A0829

(51) Int. Cl.
| | |
|---|---|
| C08B 37/00 | (2006.01) |
| A61K 31/7008 | (2006.01) |
| A61K 31/737 | (2006.01) |
| A61K 31/715 | (2006.01) |
| C08L 5/08 | (2006.01) |

(52) U.S. Cl.
CPC .............. *C08L 5/08* (2013.01); *A61K 31/715* (2013.01); *A61K 31/737* (2013.01); *C08B 37/0069* (2013.01)

(58) Field of Classification Search
CPC ........................ C08B 37/0069; A61K 31/7008
USPC ............................ 536/53, 55.2, 55.1; 514/62
See application file for complete search history.

(56) References Cited

U.S. PATENT DOCUMENTS

| | | |
|---|---|---|
| 4,704,356 A | 11/1987 | Thonar |
| 6,777,398 B2 | 8/2004 | Zoppetti et al. |
| 2010/0063001 A1 | 3/2010 | Jolly et al. |

OTHER PUBLICATIONS

Volpi, Nicola, Quality of Different Chondroitin Sulfate Preparations in Relation to their Therapeutic Activity, Journal of Pharmacy and Pharmacology, 2009, 1271-1280, vol. 61.
Volpi, Nicola, Analytical Aspects of Pharmaceutical Grade Chondroitin Sulfates, Journal of Pharmaceutical Sciences, Dec. 2007, 3168-3180, vol. 96, Issue 12.
D'Arcy, S. M. et al., Preliminary Investigation into the Purification, NMR Analysis, and Molecular Modeling of Chondroitin Sulphate Epitopes, Carbohydrate Research, 1994, 41-59, vol. 255.
Hardingham, T. E. et al., The Sulphation Pattern in Chondroitin Sulphate Chains Investigated by Chondroitinase ABC and ACII Digestion and Reactivity with Monoclonal Antibodies, Carbohydrate Research, 1994, 241-254, vol. 255.
Chai, W. et al., Generation and Structural Characterization of a Range of Unmodified Chondoitin Sulfate Oligosaccharide Fragments, Analytical Biochemistry, 1996, 88-102, vol. 237.
Zaia, J. et al., Tandem Mass Spectrometric Determination of the 4S/6S Sulfation Sequence in Chondoitin Sulfate Oligosaccharides, Analytical Chemistry, 2001, 6030-6039, vol. 73.
Desaire, H. et al., Evidence of Block and Randomly Sequenced Chondroitin Polysaccharides: Sequential Enzymatic Digestion and Quantification Using Ion Trap Tandem Mass Spectrometry, Analytical Chemistry, 2001, 3513-3520, vol. 73.
Kimata, K. et al., Cytodifferentiation and Proteoglycan Biosynthesis, Molecular and Cellular Biochemistry, Jun. 1973, 211-228, vol. 1, No. 2.
Volpi, Nicola, Influence of Charge Density, Sulfate Group Position and Molecular Mass on Adsorption of Chondroitin Sulfate onto Coral, Biomaterials, 2002, 3015-3022, vol. 23, Elsevier Science Ltd.
Volpi, Nicola et al., The Protective Effect on Cu2+ and AAPH-Mediated Oxidation of Human Low-Density Lipoproteins Depends on Glycosaminoglycan Structure, Biochimie, 1999, 955-963, vol. 81.
Volpi, Nicola, Adsorption of Glycosaminoglycans onto Coral—A New Possible Implant Biomaterials for Regeneration Therapy, Biomaterials, 1999, 1359-1363, vol. 20, Elsevier Science Ltd.
Suzuki, Sakaru et al., Formation of Three Types of Disulfated Disaccharides from Chondroitin Sulfates by Chondroitinase Digestion, The Journal of Biological Chemistry, 1968, 1543-1550, vol. 243, Issue 7.
Jordan, K.M. et al., EULAR Recommendations 2003: An Evidence Based Approach to the Management of Knee Osteoarthritis: Report of a Task Force of the Standing Committee for International Clinical Studies Including Therapeutic Trials (ESCISIT), Ann Rheum Dis, 2003, 1145-1155, vol. 62.
Zhang, W. et al., EULAR Evidence Based Recommendations for the Management of Hand Osteoarthritis: Report of a Task Force of the EULAR Standing Committee for International Clinical Studies Including Therapeutics (ESCISIT), Ann Rheum Dis, 2007, 377-388, vol. 66.
McAlindon, T.E. et al., Glucosamine and Chondroitin for Treatment of Osteoarthritis: A Systematic Quality Assessment and Meta-Analysis, Journal of the American Medical Association, 2000, 1469-1475, vol. 283, Issue 11.

(Continued)

*Primary Examiner* — Patrick Lewis
*Assistant Examiner* — Everett White
(74) *Attorney, Agent, or Firm* — Amin Talati Upadhye LLP; Adam D. Sussman; George M. Carrera, Jr.

(57) ABSTRACT

A process for the preparation of a chondroitin sulphate salt with an average molecular weight (Mw) of 10-30 kDa via chemical sulphation of an unsulphated chondroitin backbone is provided. The unsulphated chondroitin can be obtained by acid hydrolysis of a capsular polysaccharide K4 made directly from *E. coli* strain O5:K4:H4 or directly produced from a genetically modified strain of *E. coli*. Sulphation of the N-acetyl-D-galactosamine residue at position 4 or 6 takes place simultaneously in the same polysaccharide chain, simulating the sulphation pattern observed in natural chondroitin sulphate.

7 Claims, 3 Drawing Sheets

(56) References Cited

OTHER PUBLICATIONS

Volpi, Nicola et al., Quantitative and Qualitative Evaluation of Chondroitin Sulfate in Dietary Supplements, Food Anal. Methods, 2008, 195-204, vol. 1.

Volpi, Nicola et al., Two Analytical Approaches to the Evaluation of Chondroitin Sulfate in European Food Supplements, Separation Science, 2009, 3-8, vol. 1, Issue 1.

Fuentes, Esteban P. et al., Oligosaccharide Mapping of Chondroitin Sulfate Obtained from Different Animal Sources, Acta Farm Bonaerense, 1998, 135-142, vol. 17, Issue 2.

Luo, X.M. et al., Chicken Keel Cartilage as a Source of Chondroitin Sulfate, Poultry Science, 2002, 1086-1089, vol. 81, Poultry Science Association, Inc.

Sugahara, Kazuyuki et al. Specificity Studies of Bacterial Sulfatases by Means of Structurally Defined Sulfated Oligosaccharides Isolated from Shark Cartilage Chondroitin Sulfate D, European Journal of Biochemistry, 1996, 865-870, vol. 239.

Lignot, B. et al., Enzymatic Extraction of Chondroitin Sulfate from Skate Cartilage and Concentration-Desalting by Ultrafiltration, Journal of Biotechnology, 2003, 281-284, vol. 103, Elseiver B.V.

Sim, Joon-Soo et al., Quantitative Analysis of Chondroitin Sulfate in Raw Materials, Ophthalmic Solutions, Soft Capsules and Liquid Preparations, Journal of Chromatography B, 2005, 133-139, vol. 818, Elsevier B.V.

Rodriguez, Maria-Luisa et al., Structure and Serological Characteristics of the Capsular K4 Antigen of *Escherichia coli* O5:K4:H4, a Fructose-Containing Polysaccharide with a Chondroitin Backbone, European Journal of Biochemistry, 1988, 117-124, vol. 177.

Volpi, "Analytical Aspects of Pharmaceutical Grade Chondroitin Sulfates," 96 J. Pharm. Sci. 12:3168-80 (2007).

Volpi, "Quality of different chondroitin sulfate preparations in relation to their therapeutic activity," J. Pharm. Pharmacol., 61:1271-1280 (2009).

Malavaki et al., "Capillary electrophoresis for the quality control of chondroitin sulfates in raw materials and formulations," Analytical Biochemistry 374: 213-220 (2008).

Moller et al., "Demonstration of immunogenic keratin sulphate in commercial chondroitin 6-sulphate from shark cartilage. Implications for ELISA assays," Clinica Chimica Acta 236:195-204 (1995).

Pomin et al., "Residual keratan sulfate in chondroitin sulfate formulations for oral administration," Carbohydrate Polymers 90:839-846 (2012).

Galeotti et al., "Selective removal of keratan sulfate in chondroitin sulfate samples by sequential precipitation with ethanol," Analytical Biochemistry 448:113-115 (2014).

Bedini, E. et al., "Microbiological-chemical strategy to produce chondroitin sulfate A,C," Angewandt Chemie International Edition, vol. 50, No. 27, 2011, p. 6160-6163.

Khan, R. et al., "Selective acetylation reactions of hyaluronic acid benzyl ester derivative," Carbohydrate Research, vol. 306, No. 1-2, 1998, p. 137-146.

Habuchi, "Diversity and functions of glycosaminoglycan sulfotransferases," Biochimica et Biophysica Acta, 2000, 1474, pp. 115-127.

Honke et al., "Sulfotransferases and Sulfated Oligosaccharides," Medicinal Research Reviews, 2002, vol. 22 No. 6, pp. 637-654.

Kusche-Gullberg et al., "Sulfotransferases in glycosaminoglycan biosynthesis," Current Opinion in Structural Biology, 2003, 13:605-611.

DeAngelis, "Evolution of Glycoasminoglycans and Their Glycosyltransferases: Implications for the Extracellular Matrices of Animals and the Capsules of Pathogenic Bacteria," The Anatomical Record, 2002, 268:317-326.

BIOTECHNOLOGICAL SULPHATED CHONDROITIN SULPHATE AT POSITION 4 OR 6 ON THE SAME POLYSACCHARIDE CHAIN, AND PROCESS FOR THE PREPARATION THEREOF

The present invention relates to a method for the production of chondroitin sulphate by chemical sulphation starting from an unsulphated chondroitin backbone. The process according to the invention allows simultaneous sulphation, within the same polysaccharide chain, of position 4 or position 6 of the N-acetyl-D-galactosamine residue. The chondroitin sulphate thus obtained presents the same sulphation pattern as observed in natural chondroitin sulphate, unlike that obtained with the synthesis methods described so far.

BACKGROUND

Chondroitin sulphate (CS) is a complex natural polysaccharide belonging to the glycosaminoglycan (GAG) class, consisting of disaccharide sequences formed by residues of glucuronic acid (GlcA) and N-acetyl-D-galactosamine (GalNAc) sulphated in different positions and bonded by beta 1-3 bonds.

CS is present in animal tissues, with structural and physiological functions. Depending on its origin, CS mainly consists of variable percentages of two types of disaccharide unit monosulphated at position 4 or position 6 of GalNAc (disaccharides A and C respectively). However, disaccharides in which the sulphate groups are present in different numbers and different positions may be present in various percentages in the polysaccharide chains. The CS backbone also contains unsulphated disaccharide, generally in small quantities. Disulphated disaccharides having two sulphate groups bonded through the oxygen atom in various positions, such as position 2 of GlcA and 6 of GalNAc (disaccharide D), position 2 of GlcA and 4 of GalNac, or positions 4 and 6 of GalNAc (disaccharide E), can be present in the CS backbone in variable percentages, depending on the specific animal sources (Volpi N. J Pharm Pharmacol 61, 1271, 2009. Volpi N. J Pharm Sci 96, 3168, 2007. Volpi N. Curr Pharm Des 12, 639, 2006).

The repeating disaccharide unit found in CS has the following chemical formula:

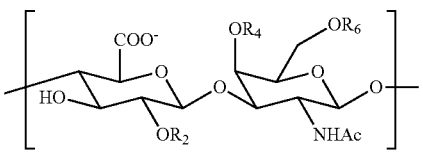

wherein $R_2$, $R_4$ and $R_6$ are independently H or $SO_3^-$.

The negative charges of the carboxylate and sulphate groups in the repeating disaccharide unit are neutralised by sodium ions.

The meanings of the acronyms most commonly used to identify the variously sulphated disaccharides are set out below:

| | |
|---|---|
| Di-0S | ($R_2$ = H; $R_4$ = H; $R_6$ = H) |
| Di-6S (C) | ($R_2$ = H; $R_4$ = H; $R_6$ = $SO_3^-$) |
| Di-4S (A) | ($R_2$ = H; $R_4$ = $SO_3^-$; $R_6$ = H) |
| Di-4,6diS (E) | ($R_2$ = H; $R_4$ = $SO_3^-$; $R_6$ = $SO_3^-$) |
| Di-2,6diS (D) | ($R_2$ = $SO_3^-$; $R_4$ = H; $R_6$ = $SO_3^-$) |
| Di-2,4diS (B) | ($R_2$ = $SO_3^-$; $R_4$ = $SO_3^-$; $R_6$ = H) |
| Di-2,4,6triS | (R2 = $SO_3^-$; $R_4$ = $SO_3^-$; $R_6$ = $SO_3^-$) |

Samples of CS originating from different animal sources are also characterised by different molecular weights and charge densities, this latter parameter being directly correlated with the specific sulphated groups.

Table 1 shows the main disaccharides found in natural CS extracted from cartilage and other tissues of various animal species:

TABLE 1

| | Bovine CS | Porcine CS | Chicken CS | Shark CS | Skate CS | Squid CS |
|---|---|---|---|---|---|---|
| Mn (kDa) | 12-17 | 9-14 | 8-13 | 25-40 | 27-34 | 60-80 |
| Mw (kDa) | 20-26 | 14-20 | 16-21 | 50-70 | 50-70 | 80-120 |
| Polydispersity index | 1.8-2.2 | 1.4-1.8 | 1.6-2.0 | 1.0-2.0 | 1.2-2.5 | 0.8-1.3 |
| Di-0S | 6 | 6 | 8 | 3 | 3 | 13 |
| Di-6S | 33 | 14 | 20 | 44 | 39 | 15 |
| Di-4S | 61 | 80 | 72 | 32 | 43 | 50 |
| Di-2,6diS | ND | ND | ND | 18 | 13 | 0 |
| Di-4,6diS | ND | ND | ND | 2 | 1 | 22 |
| Di-2,4diS | ND | ND | ND | 1 | 1 | 0 |
| Charge density | 0.90-0.96 | 0.92-0.96 | 0.90-0.94 | 1.15-1.25 | 1.08-1.20 | 1.00-1.20 |
| Ratio 4S/6S | 1.50-2.00 | 4.50-7.00 | 3.00-4.00 | 0.45-0.90 | 1.00-1.40 | 2.50-4.00 |

Mn = number average molecular weight;
Mw = weight average molecular weight;
Polydispersity Index = Mw/Mn;
Charge Density = the number of sulphate groups per disaccharide units;
ND = Not identified.

As shown in Table 1, CS derived from land animals has similar molecular mass parameters (Mn and Mw), whereas it is different from that originating from fish species, which have higher molecular mass values. The terrestrial CS samples are also characterised by charge density (CD) values below 1.0, whereas the marine CS samples always have CD values exceeding 1.0. This characteristic is due to the different distribution of the sulphated disaccharides. Generally, disulphated disaccharides are found in trace amounts in terrestrial CS, and no polysulphated disaccharides (tri- and tetra-sulphates) are observed in natural CS.

The absence of tri- and tetra-sulphated disaccharides can easily be evidenced by analysis following digestion of the polysaccharide with chondroitinase ABC, a lytic enzyme specific for monosulphated disaccharides (Di-4S and Di-6S) and for unsulphated disaccharides (Di-0S), which are able to digest disulphated disaccharides but unable to hydrolyse the polysaccharide chain in correspondence with the polysulphated disaccharides. FACE (Fluorophore-Assisted Carbohydrate Electrophoresis) analysis of natural CS digested with chondroitinase ABC does not detect the electrophoresis bands characteristic of the partly undigested oligosaccharides which are found in synthetic or semisynthetic CS deriving from the prior art.

It is also well known that, due to biosynthesis processes, all natural CSs always show the simultaneous presence of monosulphated disaccharides at position 4 or 6 of GalNAc on the same polysaccharide chains (D'Arcy, S. M. et al., Carbohydr. Res., Vol. 255, Mar. 4, 1994, pp. 41-59; Hardingham, T. E. et al., Carbohydr. Res., Vol. 255, Mar. 4, 1994, pp. 241-54; Cheng, F. et al., Glycobiology, Vol. 2, No. 6, December 1992, pp. 553-61; Chai, W. et al., Anal. Biochem., Vol. 237, No. 1, May 15, 1996, pp. 88-102; Zaia, J. et al., Anal Chem., Vol. 73, No. 24, Dec. 15, 2001, pp. 6030-39; Desaire, H. et al., Anal Chem., Vol. 73, No. 15, Aug. 1, 2001, pp. 3513-20).

Different activities have been reported for CS in relation to its molecular structure (Kimata, K. et al., Mol. Cell. Biochem., Vol. 1, 1963, p. 211; Volpi, N., Biomaterials, Vol. 23, 2002, p. 3015; Volpi, N. and Tarugi, P., Biochimie, Vol. 81, 1999, p. 955; Volpi, N., Biomaterials, Vol. 20, 1999, p. 1359; Suzuki, S. et al., J. Biol. Chem., Vol. 243, 1968, p. 7).

CS has anti-inflammatory activity, and is currently recommended in the treatment of osteoarthritis (OA) as a Symptomatic Slow-Acting Drug for OsteoArthritis (SYSADOA) in Europe, in particular for the treatment of osteoarthritis of the knee (Jordan, K. M. et al., Ann. Rheum. Dis., Vol. 62, 2003, p. 1145), hip (Jordan, K. M. et al., Ann. Rheum. Dis., Vol. 62, 2003, p. 1145) and hand (Zhang, W. et al., Ann. Rheum. Dis., Vol. 66, 2007, p. 377) on the basis of clinical evidence and corresponding meta-analyses of numerous clinical trials. CS is also widely used as a nutraceutical in Europe and the USA, either alone or in combination with other ingredients (McAlindon, T. E. et al., JAMA, Vol. 283, 2000, p. 1469; Volpi, N. et al., Food Anal. Meth., Vol. 1, 2008, p. 195; Volpi, N. et al., Separation Sc., Vol 1, 2009, p. 22).

Commercial CS is obtained by extraction from animal tissue, such as bovine and porcine tissue (Fuentes, E. P. et al., Acta Farm. Bonaerense, Vol. 17, 1998, p. 135), bird tissue (Luo, X. M. et al., Poult. Sci., Vol. 81, 2002, pp. 1086-89) and fish cartilage (Sugahara, K. et al., Eur. J. Biochem., Vol. 239, 1996, p. 871; Lignot, B. et al., J. Biotechnol., Vol. 103, 2003, p. 281).

The animal origin of commercial CS involves safety problems associated with transmissible infectious agents that cause diseases such as bovine spongiform encephalopathy (BSE), and restricts the possible sources available to meet the growing worldwide demand. These factors have stimulated research into alternative methods of producing CS.

Intensive efforts have been made to find a biotechnological method of producing CS, using a micro-organism as source of a precursor polysaccharide which has a structure partly similar to that of CS and conducting chemical sulphation to produce a CS similar to the natural one.

One example of this strategy is the production of biotechnological CS from capsular polysaccharide K4 of E. coli O5:K4:H4, as described in EP 1304338 B1. Said patent discloses a process wherein polysaccharide K4 produced in liquid cultures is extracted and purified, and then redissolved and subjected to acid hydrolysis to eliminate the fructose residues bonded to the GlcA residues of the polymer. The defructosylated polymer, identical to the unsulphated backbone of CS(CH), is then sulphated at position 4 or position 6 of the GalNAc residue according to two different chemical synthesis methods. Said patent also discloses a third method whereby a disulphated CS in both positions 4 and 6 is obtained. The CS described therein has a content of at least 70% of sulphated polysaccharides consisting of mono- and/or di-sulphated at position 4 and 6 of the GalNAc residue, position 2' of the GlcA residue being unsulphated, and has a molecular weight (Mw) of 6-25 kDa and a charge density (CD) of 0.7-2.0.

In EP 1304338 B1 the authors disclose and claim, depending on the synthesis strategy used, the possibility of:

(a) synthesising CS 4S by selectively protecting position 6 of all the N-acetylgalactosamine (GalNAc) residues present, thus obtaining a polymer selectively sulphated only at position 4 of all the N-acetylgalactosamine (GalNAc) residues; and (b) obtaining a polymer in which, similarly, the hydroxyl groups at position 6 of all the GalNAc residues are sulphated, suitably protecting the hydroxyl residues present at position 4.

In the process described in EP 1304338 B1, simultaneous sulphation therefore never takes place at positions 4 or 6 in the same chain, unlike the situation with natural CS.

SUMMARY

The present invention provides, in one aspect, a process for the production of chondroitin sulphate with an average molecular weight (Mw) of 10-30 kDa by chemical sulphation starting from an unsulphated chondroitin backbone, obtained in turn by acid hydrolysis of capsular polysaccharide K4 made directly from E. coli strain O5:K4:H4, or directly produced from a genetically modified strain of E. coli. Sulphation of the N-acetyl-D-galactosamine residue at position 4 or 6 takes place simultaneously in the same polysaccharide chain, simulating the sulphation pattern observed in natural chondroitin sulphate, unlike the sulphation obtained with the synthesis methods described to date.

In another aspect a process for the preparation of chondroitin sulphate sodium salt in which all the N-acetyl-D-galactosamine units in the same polysaccharide chain are monosulphated either randomly or at the 4- or 6-position, said process including:

a) transforming a chondroitin sodium salt into its free acid or a salt thereof with a quaternary ammonium cation selected from tetramethylammonium, tetraethylammonium or tetrabutylammonium, or into the pyridinium salt or the methyl ester;

b) reacting the compound obtained in step a) with an orthoester of formula $RC(OR_1)_3$, wherein R is selected from hydrogen, methyl, ethyl or phenyl and $R_1$ is selected from methyl or ethyl, in the presence of acid catalysis, to give a compound in which the repeating disaccharide unit present in chondroitin has formula I

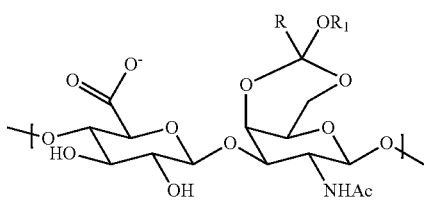

(I)

wherein R and R₁ are as defined above;

c) protecting the hydroxy groups at the 2'- and 3'-positions of the glucuronic acid units of the compound obtained in the previous step by reaction with an anhydride of formula $(R_2CO)_2O$ in which $R_2$ is selected from methyl, ethyl or propyl, in the presence of pyridine or an organic tertiary base selected from triethylamine or triisopropylamine and of 4-dimethylaminopyridine (DMAP), to give a compound in which the repeating disaccharide unit present in chondroitin has formula II

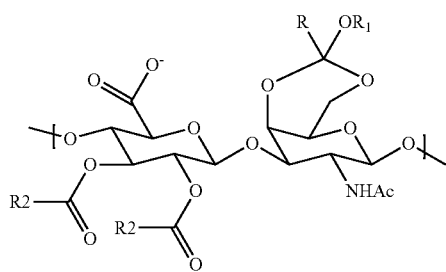

(II)

wherein R, R₁ and R₂ are as defined above;

d) rearranging the orthoester functionality present in the product obtained in step c) with an organic water-soluble acid to give an ester derivative in which the repeating GalNAc units in the polysaccharide consist of triacyl derivatives having formula IIIa

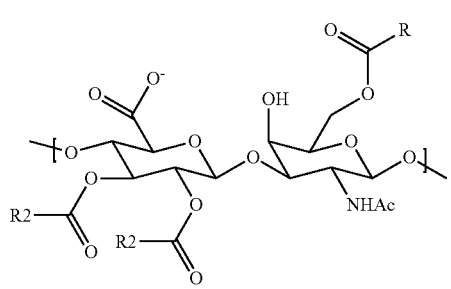

(IIIa)

or formula IIIb

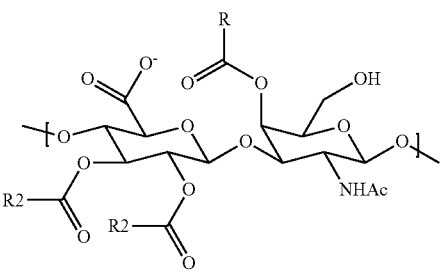

(IIIb)

wherein R and R₂ are as defined above; and e) mono-sulphating the compound obtained in step d) followed by removing the O-acyl groups present in compound IIIa or IIIb obtained in the previous step.

In further aspect, the invention comprehends a chondroitin sulphate sodium salt prepared in accordance with the methods disclosed herein and a composition including such salt. In certain embodiments, compositions including chondroitin sulphate sodium salts prepared as disclosed herein can further include one or more pharmaceutically or nutraceutically acceptable excipients.

In a still further aspect, the invention provides a method for preventing or treating osteoarthritis and/or for maintaining well-being of the musculoskeletal system including administering an effective amount of a chondroitin sulphate sodium salt prepared as disclosed herein.

The chromatogram was obtained by gradient separation on a strong anion-exchange column (SAX-HPLC) and UV detection at 232 nm. The gradient was obtained by 50 mM NaCl up to 1.2 M NaCl from 0 to 60 minutes.

Figure 2:
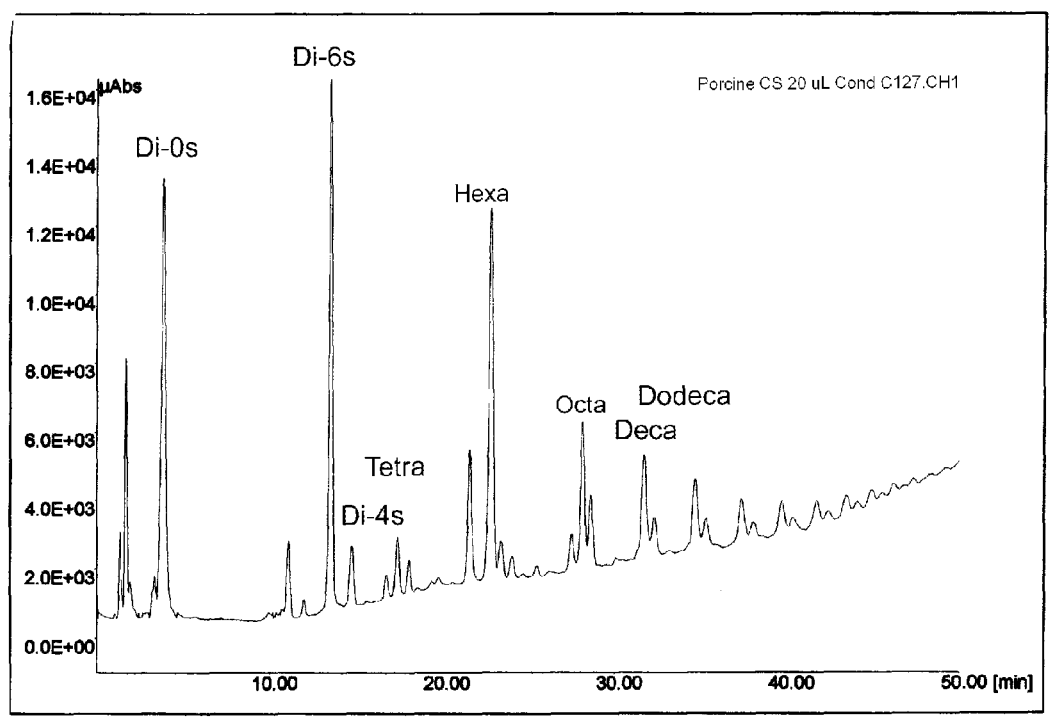

FIG. 2 relates to natural chondroitin sulphate of porcine origin treated with chondroitinase C. Various oligosaccharides of different length demonstrating the presence of sulphate groups at position 4 or 6 of the GalNAc residue on the same polysaccharide chain are formed.

The chromatogram was obtained by gradient separation on a strong anion-exchange column (SAX-HPLC) and UV detection at 232 nm.

Figure 3:
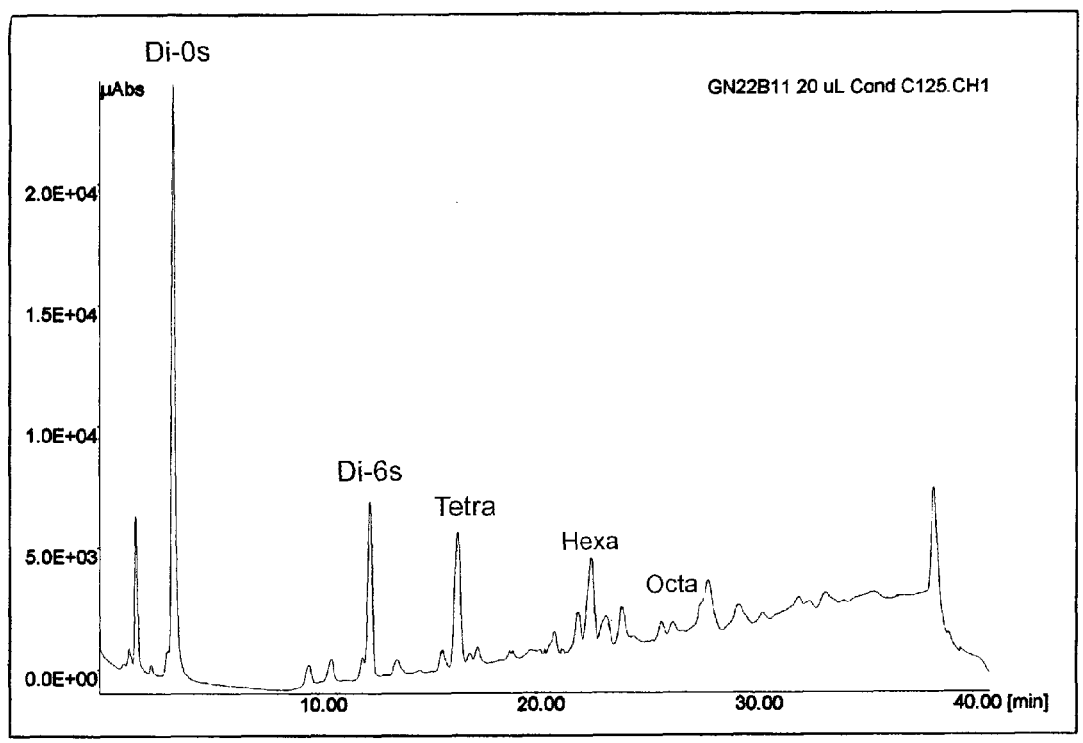

FIG. 3 relates to biotechnological chondroitin sulphate according to the present invention treated with chondroitinase C. Also for this polysaccharide various oligosaccharides of different length demonstrating the presence of sulphate groups at position 4 or 6 of the GalNAc residue on the same polysaccharide chain are formed.

The chromatogram was obtained by gradient separation on a strong anion-exchange column (SAX-HPLC) and UV detection at 232 nm.

DETAILED DESCRIPTION

The present invention describes a method for the production of CS following chemical sulphation starting from an unsulphated chondroitin backbone (CH), this CH being obtained by acid hydrolysis of a natural microbial polysaccharide i.l. (K4), or produced directly from a genetically modified *E. coli*, such as *E. coli* strain DSM23644, described in patent applications MI2010A001300 and MI2010A001264. The bacterial strain described therein carries a mutation that causes the inactivation of the KfoE gene for fructosylation of K4.

The CS obtained by the process according to the invention presents the characteristics of a natural CS with a titre exceeding 95% on the basis of the analytic methods described in the European Pharmacopoeia.

The CS obtained with the process according to the invention has an average molecular weight (Mw), measured by SEC, of 10-30 kDa, preferably 20-30 kDa, and presents a distribution of mono-sulphated groups ranging from 90% of 4-sulphate and 10% of 6-sulphate to 10% of 4-sulphate and 90% of 6-sulphate (Table 2).

TABLE 2

Characteristics of the CS described in this invention

| | |
|---|---|
| Mw (kDa) | 10-30 |
| Digestibility with chondroitinase ABC | >95% |
| Di-0S | <10% |
| Di-6S | 10-90% |
| Di-4S | 90-10% |
| Di-2,6diS | <5% |
| Di-4,6diS | <5% |
| Di-2,4diS | <5% |
| Di-triS | ND |
| Di-tetraS | ND |
| Titre (w/w) | >95% |
| | (o.d.b.)* |
| Charge density | 0.8-1.0 |
| Ratio 4S/6S | 0.1-9.0 |

*o.d.b. = on dry basis

The CS obtained with the process according to the invention contains a small amount (<10%) of unsulphated disaccharide and very low percentages (<5%) of disulphated disaccharides; trisulphated disaccharides cannot be identified.

The CS obtained with the process according to the invention is characterised by charge density values of 0.8-1.0.

In some forms of implementation of the present invention, the CS obtained shows a ratio between the sulphated disaccharide at position 4 (Di-4S) and the sulphated disaccharide at position 6 (Di-6S) of less than 1, whereas in other forms it shows a ratio between (4S) disaccharide and (6S) disaccharide greater than 1.

The process according to the present invention allows site-specific sulphation to be modulated to produce a CS with a specific 4S/6S ratio within the range specified above.

One aspect of the present invention relates to the composition of the CS according to the present invention and a carrier acceptable in the pharmaceutical or nutraceutical field. Said composition can be formulated in various solid forms, such as tablets, rigid capsules, soft gelatin capsules or powdered mixtures for drinks, or in liquid forms (solutions), preferably in the form of pharmaceutical or nutraceutical preparations for parenteral or oral administration. The composition can contain other active or inactive ingredients.

The composition can also, preferably, contain at least one of the following substances: glucosamine hydrochloride, glucosamine sulphate, N-acetyl glucosamine, hyaluronic acid, heparin, keratin, dermatin, methyl sulphonyl methane, folates and reduced folates, Group B vitamins, S-adenosyl-methionine (SAMe), ascorbic acid or manganese ascorbate. The composition can be administered to patients in effective quantities based on their needs.

For example, but without limiting its use, the CS or the composition described in the present invention can be administered in a quantity of between 100 and 3000 mg daily, preferably between 1000 and 2000 mg daily, and more preferably between 1250 and 1750 mg daily, divided into two doses of approximately 600 mg or three doses of 400 mg daily.

The present invention also relates to the use of the CS described, or a composition thereof, for the treatment or prevention of osteoarthritis or for the maintenance of musculoskeletal well-being as an ingredient of a medicament or nutritional supplement.

For example, the CS described or a composition thereof can be used to make a pharmaceutical preparation, dietary additive or nutritional supplement for the prevention and/or treatment of osteoarthritis of the hip, hand or knee and the main symptoms thereof (pain, joint swelling, inflammation), Alzheimer's disease, microbial infections, arteriosclerosis and osteoporosis, and as adjuvant in antitumoral treatment and tissue regeneration, including nerve tissue.

An advantageous characteristic of the process according to the invention is that the sulphation at position 4 or 6 of the GalNAc residue takes place simultaneously in the same polysaccharide chain, simulating the sulphation pattern observed in natural CS, unlike that obtained with the synthesis methods described to date. This aspect is confirmed by the data obtained with the use of two different enzymatic systems, namely chondroitinase ABC, which is able to digest units sulphated at position 6 and position 4 and unsulphated units, and chondroitinase C, an endolyase which is able to hydrolyse in correspondence with the residues sulphated at position 6 and unsulphated residues, but unable to perform similar lytic cleavage in correspondence with the residues sulphated at position 4. The products of digestion, obtained with chondroitinase ABC and with chondroitinase C alone, are analysed with HPLC chromatography techniques, as described by Joon-Soo Sim et al. (J. Chromatography B, Vol. 818, 2005, pp. 133-39) and which are incorporated herein by reference in their entirety, qualitatively and quantitatively indicating the presence of disaccharides Di-0S, Di-4S and Di-6S and any oligosaccharides not digested by the enzymes.

Analysis of the products of digestion with chondroitinase ABC demonstrates almost total digestion of the product with formation of the unsulphated disaccharide Di-0S, monosulphated disaccharides Di-4S and Di-6S, and traces of disulphated disaccharide Di-4,6S.

Figure 1:
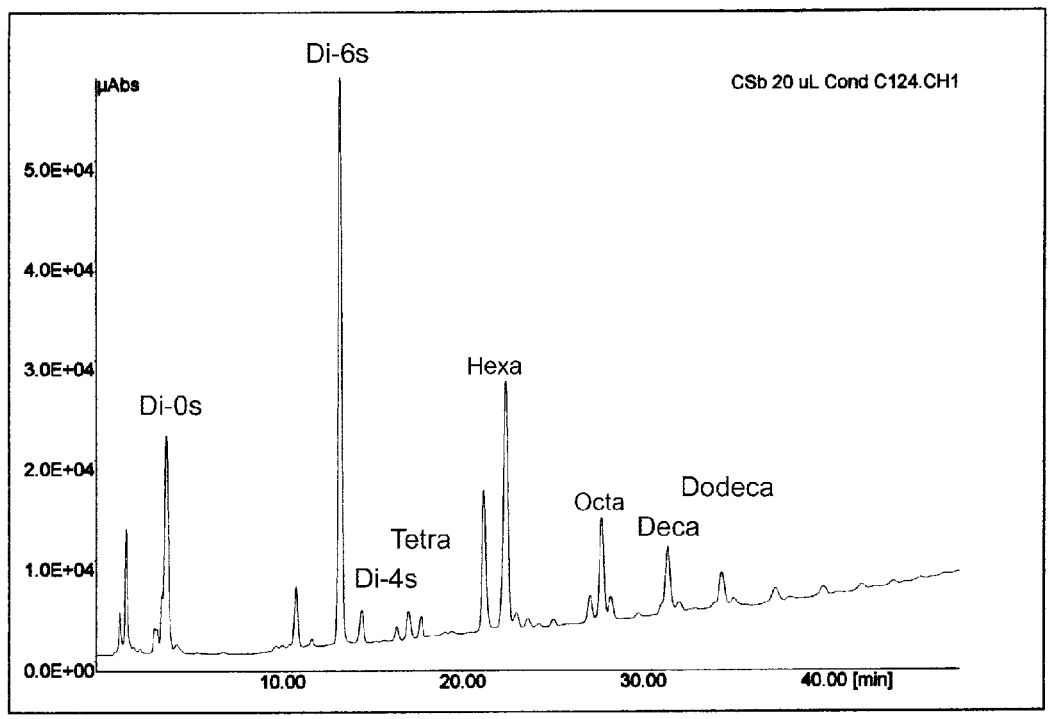
FIG. 1 relates to natural chondroitin sulphate of bovine origin treated with chondroitinase C. Various oligosaccharides of different length demonstrating the presence of sulphate groups at position 4 or 6 of the GalNAc residue on the same polysaccharide chain are formed.

However, the same analysis conducted on the products of digestion with chondroitinase C clearly shows the presence of disaccharide sequences, and above all of oligosaccharide sequences, indicating the inability of the enzyme to break down the polysaccharide completely due to the presence on the same chains of GalNAc sulphated in 4. This is because when a sulphated residue is present in 4, the enzyme is unable to act, and consequently leaves oligosaccharide residues. Said residues are also clearly detected by chromatography and electrophoresis techniques, such as gel chromatography and capillary electrophoresis (CE), as shown, for example, in the chromatographic tracings in FIGS. 1, 2 and 3 relating to digestion with chondroitinase C of natural CS (bovine and porcine) and biotechnological CS obtained according to the present invention. They contain various oligosaccharides of different lengths wherein sulphate groups are present at position 4 or 6 of the GalNAc residue on the same polysaccharide chain.

All these properties give the CS obtained with the process according to the present invention the structure of a natural CS having the following characteristics:

a) all or nearly all the GalNAc residues are monosulphated at position 6 or 4; and b) depending on the synthesis conditions used, the ratio between residues 4S and 6S (4S/6S) is completely analogous to that found in CS of both terrestrial and fish origin.

Typically, the CS according to the present invention can be obtained using as starting substrate the capsular polysaccharide K4 naturally produced by *E. coli* strain O5:K4:H4 (EP 1304338 B1) or another polysaccharide having the structure of unsulphated chondroitin (CH).

In the first case, polysaccharide K4, obtained from a culture broth of *E. coli* strain O5:K4:H4, is defructosylated at the end of fermentation by thermoacid hydrolysis, and the chondroitin is purified in accordance with an adaptation of the methods described by Rodriguez and Jann (Eur. J. Biochem., FEBS, Vol. 177, October 1988, pp. 117-24) which are incorporated herein by reference in their entirety.

Alternatively, the starting polysaccharide is obtained, for example, from the culture of *E. coli* strain DSM23644 described in MI2010A001300 which, due to a mutation induced in the KfoE gene responsible for the fructosylation of K4, produces a polysaccharide identical to natural unsulphated CH. Defructosylation is not necessary in this case; however, the thermoacid hydrolysis step is maintained to eliminate some impurities, including the bacterial endotoxins that precipitate as a result of the treatment. The chondroitin (CH) is then purified by centrifugation, dialysis and spray drying.

Hydrolysis is conducted on the culture supernatant, separated from the biomass by continuous centrifugation. Partial hydrolysis and defructosylation of K4 is performed by incubation at 90-95° C. for 30-50 min at pH 2.8-3.0.

After the incubation period, the resulting suspension is cooled at a temperature below 40° C., preferably 20-30° C., to quench the hydrolysis reaction, and the pH is simultaneously adjusted to 4-4.5. The resulting suspension undergoes, in sequence, clarification by continuous centrifugation, ultrafiltration and finally, dialysis with water through a 30 kDa membrane.

The dialysed retentate (approximately 1/10th of the volume of the initial culture broth) is filtered and finally dried with a spray dryer to obtain a polysaccharide having the structure of CH, to be subjected to the sulphation process. The CH obtained has a titre of 80-90% on a dry basis (w/w), as determined by capillary electrophoresis (CE) or HPLC.

The CH thus obtained takes the form of the sodium salt, and in order to be sulphated needs to be converted to free acid or a salt thereof.

The sulphation process according to the present invention, which allows positions 4 or 6 of the GalNAc residue of the same polysaccharide chain to be monosulphated randomly, comprises the formation of an orthoester which simultaneously involves GalNAc positions 4 and 6 and its subsequent rearrangement to an ester which, surprisingly, can be modulated to release mainly the hydroxyl in 4 or in 6, thus allowing selective sulphation of those hydroxyls.

The process according to the invention comprises the following steps:

a) Conversion of the chondroitin sodium salt to free acid or, alternatively, to a salt thereof with a quaternary ammonium ion, such as tetramethyl-, tetraethyl- or tetrabutyl-ammonium, or with pyridine. Tetrabutylammonium (TBA) salt is preferably used.

Alternatively, chondroitin (CH) in acid form is converted to its methyl ester after reaction in methanol and acetyl chloride.

b) Reaction of the chondroitin salt, or chondroitin methyl ester, with an orthoester of formula $RC(OR_1)_3$, wherein R is selected from hydrogen, methyl, ethyl or phenyl, and $R_1$ is selected from methyl or ethyl, in the presence of acid catalysis, thus obtaining a cyclic orthoester formed by the movement of two alkoxyls of the starting orthoester by alcohol functions 4 and 6 of the GalNAc residue. In the compound obtained in this step, all or nearly all the disaccharide units present possess a cyclic orthoester structure represented by formula I,

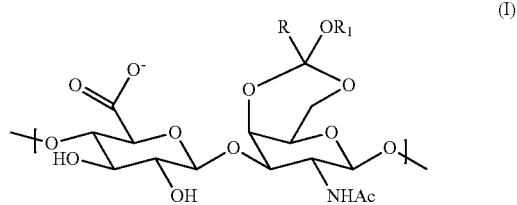

wherein R, $R_1$ are as defined above.

Examples of orthoesters which can be used are trimethyl orthoacetate, triethyl orthoacetate, trimethyl orthoformate, triethyl orthoformate, trimethyl orthopropionate, triethyl orthopropionate or trimethyl orthobenzoate. Trimethyl orthoacetate or triethyl orthoacetate is preferably used. The use of trimethyl orthoacetate is particularly preferred.

An acid selected from camphorsulphonic acid, paratoluenesulphonic acid, methanesulphonic acid or a sulphone resin, preferably camphorsulphonic acid or a sulphonic resin, more preferably camphorsulphonic acid, is used as acid catalyst.

c) Protection of the alcohol groups at positions 2' and 3' of the GlcA residue by acylation with an anhydride of a carboxylic acid of formula $(R_2CO)_2O$, wherein $R_2$ is preferably selected from methyl, ethyl or propyl in the presence of pyridine or a tertiary organic base, such as triethylamine or triisopropylethylamine, and of catalytic quantities of 4-dimethylaminopyridine (DMAP), to give a product wherein the repeating disaccharide unit found in the chondroitin has a cyclic orthoester structure acylated in 2' and 3' which is represented by formula II

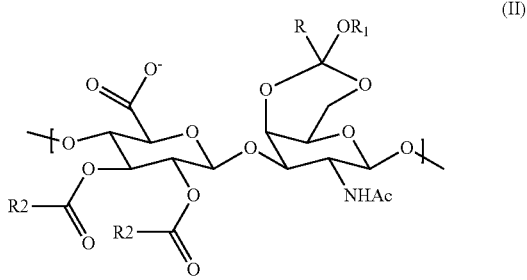

wherein R, $R_1$ and $R_2$ are as defined above.

Acetic anhydride is preferably used.

d) Rearrangement from cyclic orthoester to ester, a reaction which is performed in a mixture of a water-soluble organic acid and water, or in water only. This rearrangement, which takes place randomly on the various GalNAc units of the polysaccharide sequence, can be modulated to promote the release of one or other hydroxyl (in 4 or 6 respectively), with simultaneous formation of the ester with the soluble organic acid used in the remaining position (6 or 4 respectively). The result is the formation, in the same polysaccharide chain, of two different disaccharide units, namely:

those with a structure wherein the hydroxyls at positions 6, 2' and 3' are acylated and the hydroxyl in 4 is free, said units being represented by formula IIIa

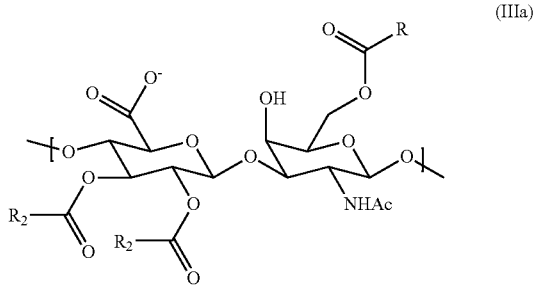

(IIIa)

wherein R and $R_2$ are as defined above; or those with a structure wherein the hydroxyls at positions 4, 2' and 3' are acylated and the hydroxyl in 6 is free, said units being represented by formula IIIb

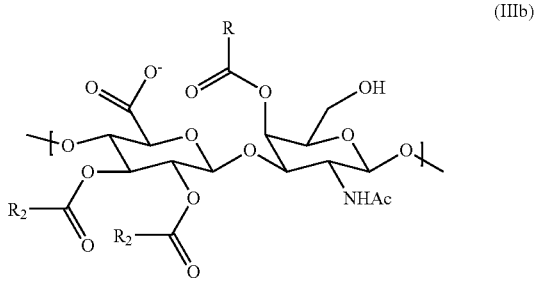

(IIIb)

wherein R and $R_2$ are as defined above.

By conducting the reaction at a temperature of between 20° and 40° C., preferably at room temperature for a time of between 1 and 48 hours, preferably between 3 and 38 hours, and more preferably for 38 hours, a larger amount of compound having the free hydroxyl in 6 is surprisingly observed, whereas when the reaction is conducted at a temperature of between 40° and 70° C., preferably 60° C., for a time of between 1 and 48 hours, preferably between 3 and 38 hours, and more preferably for 18 hours, the product with the free hydroxyl at position 4 prevails. The water-soluble organic acid is selected from acetic, formic, propionic, tartaric citric acid or a cationic resin such as for example Sepra SCX 50 μm 65A, preferably acetic acid or propionic acid, and more preferably acetic acid.

e) This is followed by sulphation with pyridine sulphur trioxide in DMF according to the method already described in EP 1304338 B1, or with the DMF-sulphur trioxide complex, to obtain a CS which, according to the rearrangement conditions used and consequently the percentage of structures IIIa and IIIb present therein, will be simultaneously and variously sulphated at position 4 of disaccharide IIIa or position 6 of disaccharide IIIb. The sulphation reaction is followed by removal, by basic treatment, of the acyl groups present at positions 2' and 3' of the GlcA residue and positions 4 or 6 of the GalNAc residue, according to the procedures described in EP 1304338 B1, giving CS sodium salt which is partly sulphated in 4 and 6.

The invention will now be further illustrated by the following examples.

Example 1: Preparation of a Tetra-Alkyl Ammonium or Pyridinium Salt of Chondroitin The CH sodium salt obtained after hydrolysis, purification and drying by the methods described above, starting from polysaccharide K4 or the polysaccharide obtained from fermentation of *E. coli* strain DSM23644, is dissolved in an aqueous medium. After complete dissolution, the solution is introduced into a column packed with a cation-exchange resin, such as Amberjet 1200 H, Rohm and Haas, or equivalent.

The fractions eluted at pH 1.5-4.0, or preferably at pH 1.5-2.0, are collected, and an aqueous solution of an ion selected from tetramethyl-, tetraethyl- and tetrabutyl-ammonium or pyridinium is added until a pH of 6.0-8.0, or preferably 6.5-7.0, is obtained. The solution is then evaporated to complete dryness by freeze-drying or spray drying to obtain the corresponding salt.

Example 2: Protection of the Hydroxylated Functions (4 and 6) of the GalNAc Portion with Formation of the Corresponding Cyclic Methyl Orthoester CH(CH-cMOE)

The salt obtained from chondroitin, such as tetrabutyl ammonium (TBA) salt, is mixed with dimethylformamide (DMF) in a flask in the quantities of 5.2 g and 130 ml respectively. 8.49 g of trimethyl orthoacetate is dripped into the flask, followed by the addition of 300 mg of camphorsulphonic acid, and the reaction mixture is maintained at 70° C. for 72 h. The reaction is then evaporated under vacuum to dryness, and further stove-dried at 40° C. for 20 h to obtain 6.1 g of chondroitin-MOE TBA in the form of a solid.

The analyses on the product of reaction were conducted to confirm that protection had taken place. The disappearance of the starting product and the appearance of a new product with a higher molecular weight (48 KDa) was established with SEC-HPLC. The analyses performed by digestion with chondroitinase ABC, an enzyme able to hydrolyse free but not protected CH, demonstrated that the unprotected percentage of starting CH molecules was under 15%.

Example 3: 2',3' Acetylation of Chondroitin Cyclic Orthoester (2',3'diacetyl CH-cMOE)

The chondroitin originating from the preceding step, protected as cyclic methyl orthoester (CH-cMOE) (4.79 g), is introduced into a reaction flask with 23.95 ml of acetonitrile, 15.69 ml of triethylamine (TEA), 6.21 ml of acetic anhydride and 78.96 mg of 4-dimethylaminopyridine (DMAP). After 2 hours'stirring at 25°-26° C., 94 ml of di-isopropyl ether is added to obtain a viscous solid, which is then filtered through filter paper and stove-dried under vacuum at 45° C. for 24 h. The intermediate cyclic orthoester thus obtained has the appearance of a pink solid.

Example 4: Rearrangement from Cyclic Methyl Orthoester to Ester with Prevalent Formation of Acetate at Position 4, and with the Free Hydroxyl at Position 6 (See Formula IIb)

The intermediate obtained from the preceding step (2.42 g) is introduced into a reaction flask, to which 18.8 ml of 96% acetic acid and 2.35 ml of demineralised water are added. The mixture is stirred for 38 h at room temperature, after which 100 ml of an 0.6 M solution of NaCl are added and the mixture is ultrafiltered through a 5 kDa membrane and dialysed, to recover a retentate with a pH of 3.32.

The solution is evaporated under vacuum at 45°-50° C.; after further stove-drying overnight, 1.38 g of a product with the appearance of a vitreous solid are obtained.

Example 5: Rearrangement from Cyclic Methyl Orthoester to Ester with Prevalent Formation of the Acetate at Position 6, and with the Free Hydroxyl at Position 4 (See Formula IIIa)

2.42 g of intermediate cyclic orthoester obtained from the preceding step are introduced into a reaction flask with 14.52 ml of 96% acetic acid and 9.8 ml of demineralised water and heated to 60° C. for 17.5 h, 100 ml of 0.6 M NaCl are then added and the solution (pH 2.27) is ultrafiltered and dialysed to recover a retentate with a pH of 3.56.

The solution is evaporated under vacuum at 45°-50° C., and after further stove-drying overnight, 1.12 g of a product with the appearance of a vitreous solid are obtained.

Example 6: Preparation of Chondroitin Sulphate with Sulphur Trioxide Pyridinium Complex The intermediate obtained as described in Example 4 (0.76 g) is introduced into a flask with 46.0 ml of DMF starring the mixture at 30° C. for 10 min. 0.72 g of sulphur trioxide pyridinium are added and when the starting material has dissolved (approximately 10 min), the solution is left under stirring at 30° C. for 1 h. A further 0.72 g of sulphur trioxide pyridinium are then added, followed by a further 0.72 g of sulphur trioxide pyridinium. The solution is stirred for a further hour at 30° C.

The reaction is quenched by pouring the mixture into 50 ml of 10% NaHCO$_3$ in water at room temperature (pH 7.81). After filtration the solution is evaporated under vacuum (10 mBar) to dryness, the residue redissolved with 150 ml of 0.6 M NaCl and, finally, the solution is ultrafiltered.

After 6 changes of volume the retentate has a pH of 9.22; the pH is adjusted to 6.7 with 1N HCl and ultrafiltration continues, replacing the 0.6N NaCl solution with demineralised water.

The resulting solution is ultrafiltered again for 2 volumes, and then dialysed to a volume of 20 ml. The dialysed solution is concentrated to dryness under vacuum (10 mBar, 45° C.).

The product thus obtained (0.88 g) is dissolved with 34.0 ml of 0.2N soda (NaOH) and heated to 40° C. under stirring for 2 h. Finally, the solution is diluted with an 0.6M aqueous solution of sodium chloride, ultrafiltered through a 5 kDa membrane, and dialysed with demineralised water. The retentate is concentrated to dryness under vacuum (45° C., 10 mBar), to obtain 0.67 g of chondroitin sulphate. The end product, which has a molecular weight of 29 kDa, determined by HPLC-SEC, shows:
  digestibility with chondroitinase ABC exceeding 95%;
  a 4S/6S ratio of 18/82;
  a total charge density value of approximately 0.9; and
  only partial digestibility with chondroitinase C, demonstrated by the presence of oligosaccharides due to the presence on the same polysaccharide chain of both 4-sulphated and 6-sulphated units, characteristic of the present invention.

Example 7: Preparation of Chondroitin Sulphate with Sulphur Trioxide Pyridinium Complex The intermediate obtained as described in example 5 (1.12 g) is introduced into a flask with 67.2 ml of DMF, stirring the mixture at 50° C. for 10 min. 1.05 g of sulphur trioxide pyridinium are added, and when the starting material has dissolved (approximately 10 min), the solution is left under stirring at 50° C. for 1 h. A further 1.05 g of sulphur trioxide pyridinium are then added. The solution is stirred for a further hour at 50° C.

The reaction is quenched by pouring the mixture into 60 ml of 10% NaHCO$_3$ in water at room temperature (RT) (pH 7.81). After filtration the solution is evaporated under vacuum (10 mBar) to dryness, and the residue is redissolved with 30 ml of 0.6 M NaCl. Finally, the solution is ultrafiltered.

After 6 changes of volume the retentate has a pH of 9.22; the pH is adjusted to neutrality (7.5) with 1 N HCl and microfiltration continues, replacing the 0.6 N NaCl solution with demineralised water.

The resulting solution is ultrafiltered again for 2 volumes, and then dialysed to a volume of 20 ml. The dialysed solution is concentrated to dryness under vacuum (10 mBar, 45° C.), to obtain 1.53 g of product.

This residue is dissolved in 59.6 ml of 0.2 N soda (NaOH) and heated at 60° C. for 2 h. Finally, the solution is diluted with an 0.6M aqueous solution of sodium chloride, ultrafiltered through a 3 kDa membrane, and dialysed with demineralised water. The retentate is concentrated to dryness under vacuum (45° C., 10 mBar), to obtain 0.76 g of chondroitin sulphate.

The product thus obtained has a molecular weight of 15.4 kDa, determined by HPLC-SEC; digestibility with chondroitinase ABC exceeding 95%; a 4S:6S ratio of 82:18; and a total charge density value of approximately 1.09. The almost complete digestion obtained with chondroitinase ABC (over 95% of the product is broken down), together with reduced digestibility with chondroitinase C, which are characteristic of the present invention, demonstrate the existence of both 4-sulphated and 6-sulphated units on the same polysaccharide chain.

Over 95% digestibility with chondroitinase ABC also demonstrates the absence of polysulphated (tri- and tetrasulphated) disaccharides in the CS polysaccharide chain to which the present invention relates.

Example 8: Preparation of Chondroitin (Ch) Methyl Ester 10.0 g of CH in acid form are added to a solution of 1.3 L of methanol and 14.43 g of acetyl chloride placed under stirring at room temperature for 2 hours in a 3 liter flask, and the suspension obtained is left under stirring for 20 hours.

When that time has elapsed, the suspension is filtered and the solid is washed with 100 ml of methanol (2×50 ml) and dried at 50° C. under vacuum to recover 9.4 g of dry solid.

The reaction is repeated a second time with the same procedure, and when the second period has elapsed, the suspension is cooled at between 0° and 5° C. for 60 minutes before filtration. The solid obtained is washed with cold methanol (0-5° C.) and stove-dried under vacuum for 3 hours at 50° C. to recover 6.3 g of solid.

Example 9: Protection of the Hydroxylated Functions (4 and 6) of the GalNAc Portion of CH Methyl Ester by Orthoester Formation 150 ml of dimethylformamide (DMF) and 6.0 g of the product obtained in the preceding step are introduced into a 500 ml flask with a calcium chloride valve and nitrogen flow. 20.06 g of trimethyl orthoacetate and 0.71 g of camphorsulphonic acid are then added. The solution obtained is heated at 50° C. (internal temperature) for 18 hours.

At the end of that period it is left to cool at RT and concentrated under vacuum to obtain 8.5 g of product.

Example 10: Acetylation of the 2',3' Hydroxyls of the Product Deriving from Example 9

8.0 g of the product obtained in the preceding step, 40 ml of DMF, 28.6 g of triethylamine, 17.15 g of acetic anhydride and 96 mg of dimethylaminopyridine are introduced into a 250 ml flask with a calcium chloride valve and nitrogen flow at room temperature.

The solution obtained is left under stirring for 3 hours; when that time has elapsed, 150 ml of isopropyl ether are added to the flask and an amorphous solid precipitates. The waters are eliminated by decanting and 100 ml of isopropyl ether are added to the solid and left under stirring for 1 hour. The solid is then filtered and washed with 50 ml of isopropyl ether and dried under vacuum at 40° C. to recover 8.52 g of product.

Example 11: Rearrangement of Orthoester Deriving from Example 10

7.0 g of the product obtained in the preceding step, 72.8 g of glacial acetic acid and 8.7 ml of water are introduced into a 250 ml flask to obtain a solution which is left under stirring at RT for 3 hours. The solution is then diluted to 150 ml with 0.6 M sodium chloride and the resulting solution is purified by ultrafiltration through a 5 KD membrane. After dialysis, the solution obtained is concentrated under vacuum and 6.7 g of solid product are recovered.

Example 12: Sulphation of Triacetyl Methyl Ester 670 mg of the product obtained in the preceding step are introduced into a 250 ml flask with nitrogen flow and calcium chloride valve with 40 ml of DMF.

630.44 g of sulphur trioxide pyridinium complex are added to the solution obtained and the resulting solution is heated at 50° C. (internal temperature) for 1 hour. 630.44 g of sulphur trioxide pyridinium complex are then added to the flask at the same temperature and again left under stirring for 1 hour.

When that time has elapsed, the solution is cooled to RT and 40 ml of 3% NaHCO$_3$ are added to the flask at the same temperature to produce a solution which is concentrated under vacuum to obtain 2.3 g of solid mixed with inorganic salts. The product obtained is diluted to 150 ml of 0.6 M sodium chloride and ultrafiltered through a 5 KDa membrane.

After dialysis, the solution obtained is concentrated under vacuum and 1.32 g of solid product are recovered.

Example 13: To Obtain Chondroitin Sulphate

The product obtained in the preceding step is introduced into a 100 ml flask with 33 ml of 0.2 M soda. The solution is heated at 40° C. (internal temperature) for 2 hours, after which it is cooled to RT and neutralised with 1M HCl.

The solution is diluted to 150 ml of 0.6 M sodium chloride and ultrafiltered through a 5 KDa membrane. After dialysis and concentration of the solution under vacuum, 350 mg of solid are obtained.

The product obtained in this example has a molecular weight of 11 KDa, a 4S:6S ratio of 47:53, and a charge density value of 0.9.

The invention claimed is:
1. Triacyl derivatives of formulae IIIa and IIIb of repeating N-acetyl-D-galactosamine (GalNAc) units in a polysaccharide chain, wherein the triacyl derivatives of formulae IIIa and IIIb are prepared by selective release from a cyclic orthoester compound of a hydroxyl group at the 6-position or at the 4-position, respectively, the process comprising:
   a) transforming a chondroitin sodium salt, obtained from a polysaccharide produced by a culture broth of *E. coli* strain DSM23644, into its free acid or a salt thereof with a quaternary ammonium cation selected from the group consisting of tetramethylammonium, tetraethylammonium, and tetrabutylammonium, into a pyridinium salt, or into a methyl ester;
   b) reacting the compound obtained in step a) with an orthoester of formula RC(OR$_1$)$_3$, wherein R is selected from hydrogen, methyl, ethyl or phenyl and R$_1$ is selected from methyl or ethyl, in the presence of acid catalysts, to give a cyclic orthoester compound in which a repeating disaccharide unit present in chondroitin has the formula I

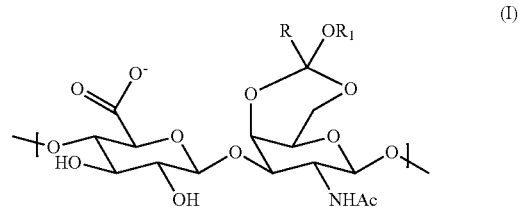

wherein R and R$_1$ are as defined above;
   c) protecting the hydroxy groups at the 2'- and 3'-positions of the glucuronic acid units of the compound obtained in step b) by reacting the compound with an anhydride of formula (R$_2$CO)$_2$O, wherein R$_2$ is selected from methyl, ethyl or propyl, in the presence of 4-dimethylaminopyridine (DMAP) and pyridine or an organic tertiary base selected from triethylamine or triisopropylamine, to give a compound in which a repeating disaccharide unit present in chondroitin has formula II

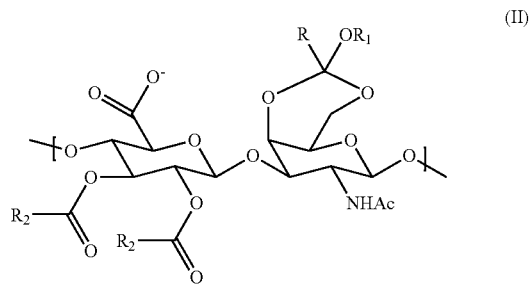

wherein R, R$_1$ and R$_2$ are as defined above;
   d) rearranging the cyclic orthoester functionality present in the product obtained in step c) with an organic water-soluble acid to give the triacyl derivatives of formulae IIIa

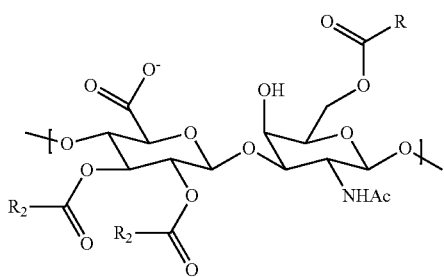

(IIIa)

and formula IIIb

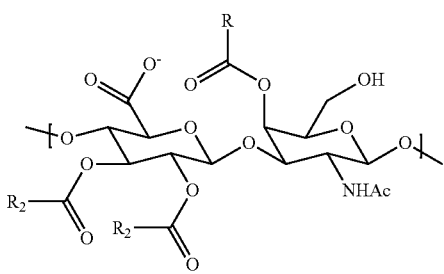

(IIIb)

wherein R and $R_2$ are as defined above; and wherein the triacyl derivatives of formulae IIIa and IIIb are prepared in a desired ratio in a polysaccharide chain.

2. The triacyl derivatives of formulae IIIa and IIIb prepared according to the process of claim 1, wherein the desired ratio in a polysaccharide chain of the prepared triacyl derivatives of formulae IIIc and IIIb is 18:82.

3. The triacyl derivatives of formulae IIIa and IIIb of claim 1, wherein the desired ratio in a polysaccharide chain of the prepared triacyl derivatives of formulae IIIc and IIIb is 82:18.

4. The triacyl derivatives of formulae IIIa and IIIb of claim 3, wherein the triacyl derivatives were prepared in a reaction conducted at a temperature of between 45° and 70° C.

5. The triacyl derivatives of formulae IIIa and IIIb of claim 3, wherein the triacyl derivatives were prepared in a reaction conducted for a time of about 18 hours.

6. The triacyl derivatives of formulae IIIa and IIIb of claim 2, wherein the triacyl derivatives were prepared in a reaction conducted at a temperature of between about 20° and 40° C.

7. The triacyl derivatives of formulae IIIa and IIIb of claim 2, wherein the triacyl derivatives were prepared in a reaction conducted for a time of about 38 hours.

* * * * *

UNITED STATES PATENT AND TRADEMARK OFFICE
CERTIFICATE OF CORRECTION

Page 1 of 1

PATENT NO. : 9,718,947 B2
APPLICATION NO. : 13/270435
DATED : August 1, 2017
INVENTOR(S) : Davide Bianchi et al.

It is certified that error appears in the above-identified patent and that said Letters Patent is hereby corrected as shown below:

In the Claims

In Claim 2, Column 18, Line 8, change "IIIc" to --IIIa--.

In Claim 3, Column 18, Line 11, change "IIIc" to --IIIa--.

Signed and Sealed this
Seventh Day of November, 2017

Joseph Matal
*Performing the Functions and Duties of the
Under Secretary of Commerce for Intellectual Property and
Director of the United States Patent and Trademark Office*